United States Patent
Stibich (10) Patent No.: US 11,648,326 B2
(45) Date of Patent: May 16, 2023

(54) CABINETS FOR DISINFECTING OBJECTS

(71) Applicant: Xenex Disinfection Services LLC., San Antonio, TX (US)

(72) Inventor: Mark A. Stibich, Santa Fe, NM (US)

(73) Assignee: Xenex Disinfection Services Inc., San Antonio, TX (US)

(*) Notice: Subject to any disclaimer, the term of this patent is extended or adjusted under 35 U.S.C. 154(b) by 199 days.

(21) Appl. No.: 15/363,917

(22) Filed: Nov. 29, 2016

(65) Prior Publication Data

US 2017/0224858 A1    Aug. 10, 2017

Related U.S. Application Data (60) Provisional application No. 62/291,024, filed on Feb. 4, 2016.

(51) Int. Cl.
| | |
|---|---|
| *A61L 2/24* | (2006.01) |
| *A61L 2/26* | (2006.01) |
| *A61L 2/16* | (2006.01) |

(52) U.S. Cl.
CPC ............. *A61L 2/24* (2013.01); *A61L 2/16* (2013.01); *A61L 2/26* (2013.01);
(Continued)

(58) Field of Classification Search
CPC .......... A61L 2/24; A61L 2/16; A61L 2202/15; A61L 2202/14; A61L 2202/24; A61L 2202/122
See application file for complete search history.

(56) References Cited

U.S. PATENT DOCUMENTS

| | | |
|---|---|---|
| 2,615,120 A | 10/1952 | Macksoud |
| 3,418,069 A | 12/1968 | Eugene et al. |
| (Continued) | | |

FOREIGN PATENT DOCUMENTS

| | | |
|---|---|---|
| CA | 2427302 | 11/2003 |
| CN | 87203475 | 8/1988 |
| (Continued) | | |

OTHER PUBLICATIONS

UniMac brochure on UT Series 120-200 lb Tumble Dryers (Year: 2021).*

(Continued)

*Primary Examiner* — Regina M Yoo
(74) *Attorney, Agent, or Firm* — Egan, Enders & Huston LLP (57) ABSTRACT

Methods are provided which include placing one or more objects into a cabinet, subsequently closing the cabinet and remotely starting a disinfection device disposed therein to disperse a germicide within the closed cabinet. Embodiments of cabinets include an interior void of at least 10 ft³, a door to enclose the cabinet and one or more support structures arranged within the cabinet adjacent the interior void. Portions of the support structures facing the interior void are transparent and/or have through-holes. Other embodiments of cabinets include a moveable germicidal blocking partition for separating portions of the cabinet, a door for accessing one of the portions and a sensor for detecting when the partition is in position to separate the portions. An embodiment of a support structure includes a base having transparent materials and/or one or more through-holes, sidewalls shaped to match a peripheral contour of a medical device, and a weight sensor.

27 Claims, 5 Drawing Sheets

(52) U.S. Cl.
CPC ..... *A61L 2202/122* (2013.01); *A61L 2202/14* (2013.01); *A61L 2202/15* (2013.01); *A61L 2202/24* (2013.01)

(56) References Cited

U.S. PATENT DOCUMENTS

| | | | |
|---|---|---|---|
| 4,028,817 A * | 6/1977 | Winstel | D06F 58/20 |
| | | | 34/86 |
| 4,663,787 A * | 5/1987 | Kolsch | A47C 1/14 |
| | | | 5/110 |
| 4,877,964 A | 10/1989 | Tanaka et al. | |
| 4,896,042 A | 1/1990 | Humphreys | |
| 5,690,415 A * | 11/1997 | Krehl | A47F 5/101 |
| | | | 108/23 |
| 5,744,094 A | 4/1998 | Castberg et al. | |
| 5,768,853 A | 6/1998 | Bushnell et al. | |
| 5,891,399 A | 4/1999 | Owesen | |
| 5,925,885 A | 7/1999 | Clark et al. | |
| 6,165,526 A * | 12/2000 | Newman | A23L 3/0055 |
| | | | 422/24 |
| 6,242,753 B1 | 6/2001 | Sakurai | |
| 6,398,970 B1 | 6/2002 | Justel et al. | |
| 6,402,774 B1 | 6/2002 | Caldironi | |
| 6,403,030 B1 | 6/2002 | Horton, III | |
| 6,447,720 B1 | 9/2002 | Horton, III et al. | |
| 6,539,727 B1 | 4/2003 | Burnett | |
| 6,566,659 B1 | 5/2003 | Clark et al. | |
| 6,576,190 B1 | 6/2003 | Park | |
| 6,607,170 B1 | 8/2003 | Hoftman | |
| 6,656,424 B1 | 12/2003 | Deal | |
| 6,774,382 B2 | 8/2004 | Koshida | |
| 6,897,460 B2 | 5/2005 | Kobayashi et al. | |
| 6,911,177 B2 | 6/2005 | Deal | |
| 6,932,494 B1 | 8/2005 | Burnett et al. | |
| 7,175,806 B2 | 2/2007 | Deal et al. | |
| 7,282,728 B2 | 10/2007 | Culbert | |
| 7,317,393 B2 | 1/2008 | Maloney | |
| 7,329,026 B1 | 2/2008 | Hayman et al. | |
| 7,380,627 B2 | 6/2008 | Huang et al. | |
| 7,459,694 B2 | 12/2008 | Scheir et al. | |
| 7,540,998 B2 | 6/2009 | Terwilliger et al. | |
| 7,665,227 B2 * | 2/2010 | Wright | D06F 25/00 |
| | | | 34/339 |
| 7,829,867 B2 | 11/2010 | Hlavinka et al. | |
| 7,875,247 B2 | 1/2011 | Clark et al. | |
| 8,193,515 B2 | 6/2012 | Kreitenberg | |
| 8,236,236 B2 | 8/2012 | Garner | |
| 8,563,059 B2 * | 10/2013 | Luckhardt | A47J 37/00 |
| | | | 426/233 |
| 8,895,939 B2 | 2/2014 | Lyslo et al. | |
| 8,745,782 B2 * | 6/2014 | Bernat | A45F 3/24 |
| | | | 5/110 |
| 8,791,441 B1 | 7/2014 | Lichtblau | |
| 8,816,301 B2 | 8/2014 | Stibich et al. | |
| 8,872,669 B2 | 10/2014 | Stibich et al. | |
| 8,907,304 B2 | 12/2014 | Kreitenberg | |
| 9,165,756 B2 | 10/2015 | Stibich et al. | |
| 9,492,577 B1 | 11/2016 | Dayton | |
| 9,504,345 B2 | 11/2016 | Stibich et al. | |
| 9,517,284 B1 | 12/2016 | Stibich et al. | |
| 9,551,528 B2 * | 1/2017 | Kong | B25H 3/006 |
| 9,744,255 B2 | 8/2017 | Stibich et al. | |
| 9,867,894 B2 | 1/2018 | Stibich et al. | |
| 10,010,636 B2 | 7/2018 | Henniges et al. | |
| 10,154,549 B2 * | 12/2018 | Nasu | H05B 6/6473 |
| 2002/0098139 A1 | 7/2002 | Sparks | |
| 2002/0133886 A1 * | 9/2002 | Severns | B01J 20/28033 |
| | | | 8/142 |
| 2003/0048633 A1 | 3/2003 | Shiau et al. | |
| 2003/0086821 A1 | 5/2003 | Matthews | |
| 2003/0137834 A1 | 7/2003 | Jigamian et al. | |
| 2004/0052702 A1 | 3/2004 | Shuman et al. | |
| 2004/0074212 A1 | 4/2004 | Yachi et al. | |
| 2004/0151617 A1 * | 8/2004 | Zanakis | A61L 9/145 |
| | | | 422/4 |
| 2004/0175290 A1 | 9/2004 | Scheir et al. | |
| 2005/0058013 A1 | 3/2005 | Warf et al. | |
| 2005/0133740 A1 | 6/2005 | Gardner | |
| 2005/0163686 A1 | 7/2005 | Bettenhausen et al. | |
| 2006/0011397 A1 | 1/2006 | Huang et al. | |
| 2006/0159583 A1 | 7/2006 | Naslund et al. | |
| 2006/0261291 A1 | 11/2006 | Gardner | |
| 2006/0263275 A1 | 11/2006 | Lobach | |
| 2006/0284109 A1 | 12/2006 | Scheir et al. | |
| 2007/0108273 A1 * | 5/2007 | Harper | G07C 9/00896 |
| | | | 235/382 |
| 2007/0202005 A1 * | 8/2007 | Maschke | A61L 2/24 |
| | | | 422/3 |
| 2007/0255266 A1 | 11/2007 | Cumbie et al. | |
| 2007/0257205 A1 | 11/2007 | Rocha-Alvarez et al. | |
| 2008/0056933 A1 | 3/2008 | Moore et al. | |
| 2008/0253941 A1 | 10/2008 | Wichers et al. | |
| 2008/0260601 A1 | 10/2008 | Lyon | |
| 2009/0217547 A1 | 9/2009 | Kim et al. | |
| 2009/0304553 A1 | 12/2009 | Gordon | |
| 2010/0183476 A1 | 7/2010 | Lu | |
| 2010/0247403 A1 | 9/2010 | Hancock | |
| 2010/0266445 A1 * | 10/2010 | Campagna | A61L 2/10 |
| | | | 422/23 |
| 2011/0054574 A1 | 3/2011 | Felix | |
| 2011/0073774 A1 | 3/2011 | Taylor et al. | |
| 2011/0215261 A1 | 9/2011 | Lyslo et al. | |
| 2011/0305597 A1 | 12/2011 | Farren | |
| 2012/0047763 A1 | 3/2012 | Abramovich et al. | |
| 2012/0056102 A1 | 3/2012 | Stanley et al. | |
| 2012/0093688 A1 | 4/2012 | Harmon et al. | |
| 2012/0305787 A1 | 12/2012 | Henson | |
| 2012/0313532 A1 | 12/2012 | Stibich et al. | |
| 2012/0315186 A1 | 12/2012 | Davis | |
| 2013/0078142 A1 | 3/2013 | Gordon | |
| 2013/0224086 A1 | 8/2013 | Stibich et al. | |
| 2014/0060095 A1 | 3/2014 | Shur et al. | |
| 2014/0148047 A1 * | 5/2014 | Gaither | H01R 31/06 |
| | | | 439/518 |
| 2014/0158910 A1 | 6/2014 | Fletcher | |
| 2014/0161663 A1 | 6/2014 | Farren et al. | |
| 2014/0348701 A1 | 11/2014 | Kirschman | |
| 2015/0025300 A1 | 1/2015 | Hill et al. | |
| 2015/0209462 A1 | 7/2015 | Turbett et al. | |
| 2015/0314026 A1 | 11/2015 | Mauzerall et al. | |
| 2015/0359915 A1 | 12/2015 | Farren et al. | |
| 2015/0367008 A1 | 12/2015 | Romo et al. | |
| 2016/0023417 A1 * | 1/2016 | Hanson | B30B 9/3082 |
| | | | 100/99 |
| 2016/0074546 A1 | 3/2016 | Rizzone | |
| 2016/0340927 A1 * | 11/2016 | Rizzotto | E04H 15/32 |
| 2017/0051449 A1 * | 2/2017 | Nam | D06F 58/24 |
| 2017/0216472 A1 | 3/2017 | Stibich et al. | |
| 2017/0099945 A1 * | 4/2017 | Meads | A47B 67/02 |
| 2017/0216473 A1 | 8/2017 | Rizzone | |
| 2017/0368213 A1 | 12/2017 | Mintie et al. | |
| 2018/0007845 A1 | 1/2018 | Martin | |
| 2018/0207303 A1 | 7/2018 | Farren et al. | |

FOREIGN PATENT DOCUMENTS

| | | | |
|---|---|---|---|
| CN | 2678651 | 2/2005 | |
| CN | 201558350 | 8/2010 | |
| CN | 101890174 | 11/2010 | |
| CN | 201755324 | 3/2011 | |
| CN | 204864168 | 12/2015 | |
| EP | 1588720 | 10/2005 | |
| EP | 1778055 | 5/2007 | |
| FR | 2964217 A1 * | 3/2012 | ......... G06K 7/10316 |
| JP | S47-38719 B | 9/1972 | |
| JP | S55-12959 U | 1/1980 | |
| JP | H06-63108 | 3/1994 | |
| JP | H07003649 | 1/1995 | |
| JP | H09220275 | 8/1997 | |
| JP | 2000245816 | 9/2000 | |
| JP | 2006-057898 | 3/2006 | |
| JP | 2008229127 | 10/2008 | |
| JP | 2009050584 | 3/2009 | |

(56) References Cited

FOREIGN PATENT DOCUMENTS

| JP | 2012075711 | 4/2012 |
|---|---|---|
| KR | 20130000038 | 1/2013 |
| KR | 20130131958 | 12/2013 |
| KR | 1020120052521 | 5/2015 |
| WO | 01/60419 | 8/2001 |
| WO | 02/058744 | 8/2002 |
| WO | 2003/021632 | 3/2003 |
| WO | 2003021632 | 3/2003 |
| WO | 2005/082426 | 9/2005 |
| WO | 2007/008879 | 1/2007 |
| WO | 2007008879 | 1/2007 |
| WO | 2007/020282 | 2/2007 |
| WO | 2007/089312 | 8/2009 |
| WO | 2009097389 | 8/2009 |
| WO | 2010/030039 | 3/2010 |
| WO | 2010/042849 | 4/2010 |
| WO | 2011088394 | 7/2011 |
| WO | 2012085250 | 6/2012 |
| WO | 2012/142427 | 10/2012 |
| WO | 2014/022717 | 2/2014 |
| WO | 2014051906 | 4/2014 |
| WO | 2014/100493 | 6/2014 |
| WO | 2014088580 | 6/2014 |
| WO | 2015/054389 | 4/2015 |
| WO | 2015/116876 | 8/2015 |
| WO | 2016044759 | 3/2016 |
| WO | 2016073463 | 5/2016 |
| WO | 2018005104 | 1/2018 |

OTHER PUBLICATIONS terrauniversal.com, UV Sterilization/Filtration Cabinet, retrieved from internet on May 15, 2015, 1 page.
www.lumalier.com, DC Mail and Object Disinfection, retrieved from internet on May 15, 2015, 2 pages.
International Preliminsary Examining Authority, International Preliminary Report on Patentability, for PCT Application PCT/US2017/016675 dated Jun. 6, 2018, 32 pages.
International Searching Authority, Invitation to Pay Additional Fees, for PCT Application PCT/US2017/016675 dated May 31, 2017, 11 pages.
International Searching Authority, International Search Report and Written Opinion, for PCT Application PCT/US2017/016675 dated Jul. 26, 2017, 16 pages.
International Searching Authority, Written Opinion of International Preliminary Examining Authority, for PCT Application PCT/US2017/016675 dated Jan. 12, 2018, 7 pages.
International Preliminary Examining Authority, Written Opinion for International Patent Application PCT/US2017/016675 dated Apr. 24, 2018, 8 pages.
United States Patent and Trademark Office, Office Action for U.S. Appl. No. 16/052,850 dated Dec. 27, 2018, 10 pages.
European Patent Office, Communication for European Patent Application 17710077.3 dated Apr. 5, 2019, 7 pages.
European Patent Office, Summons to Oral Hearing for European Patent Application 17710077.3 dated Sep. 25, 2019, 8 pages.
European Patent Office, Intent to Grant for European Patent Application 17710077.3 dated Feb. 12, 2020, 7 pages.
Translation of Office Action for Japanese Patent Application 2018-540803 dated Apr. 9, 2019, 3 pages.
Translation of Office Action for Japanese Patent Application 2018-540803 dated Jan. 14, 2020, 5 pages.
Translation of Notice of Allowance for Japanese Patent Application 2018-540803 dated Aug. 18, 2020, 1 page.
United States Patent and Trademark Office, Office Action for U.S. Appl. No. 16/052,850 dated Jul. 12, 2019, 17 pages.
European Patent Office, Extended European Search Report for European Patent Application 20183926.3 dated Sep. 10, 2020, 11 pages.
The Xenex Training Video—2012, Xenex Every Room. Every Time.TM, dated 2012, 69 pgs.
United States Patent and Trademark Office, Office Action for U.S. Appl. No. 16/052,850 dated Jan. 23, 2020, 11 pages.
United States Patent and Trademark Office, Notice of Allowance for U.S. Appl. No. 16/052,850 dated Jan. 11, 2021, 9 pages.
European Patent Office, Communication for European Patent Application 20183926.3 dated Oct. 18, 2021, 4 pages.
Translation of Office Action for Japanese Patent Application 2020-155194 dated Nov. 9, 2021, 10 pages.
Canadian Intellectual Property Office, Office Action for Canadian Patent Application No. 3,052,574 dated Mar. 7, 2023, 6 pgs.

\* cited by examiner

CABINETS FOR DISINFECTING OBJECTS

This application is a continuation of Provisional Patent Application No. 62/291,024, filed Feb. 4, 2016.

BACKGROUND OF THE INVENTION

1. Field of the Invention

This invention generally relates to the disinfection of objects and, more specifically to, support structures, cabinets and methods for disinfecting objects.

2. Description of the Related Art

The following descriptions and examples are not admitted to be prior art by virtue of their inclusion within this section.

In general, germicidal systems are designed to subject one or more surfaces and/or objects to a germicide to deactivate or kill microorganisms residing upon the surface/s and/or object/s. Applications of germicidal systems include but are not limited to sterilization, object disinfection, and room/area decontamination. Examples of area/room decontaminations system are those used in hospital rooms to disinfect the objects therein and those used in agricultural operations, such as those which are used to breed and/or farm animals. Examples of sterilizing systems are those used for sterilizing surgical tools, food or pharmaceutical packaging. A challenge in many applications is accessing all surfaces of an object to insure thorough disinfection of the object. In particular, some germicidal systems may only effectively treat surfaces which are facing the germicidal system and, thus, surfaces not facing the system may not be disinfected adequately.

Furthermore, surfaces of an object which are in contact with a surface of another object, such as the surface of an object touching the surface of a table or surfaces of a plurality of objects stacked upon each other are hidden from exposure and, thus, such surfaces are not disinfected. Objects which are particularly susceptible for being in contact with other objects are those which are relatively small and portable. Furthermore, such objects are often handled by humans, making them more likely to have germs on their surfaces. Some germicidal systems include trays for objects to be positioned on such that access to surfaces of the objects may be manipulated. Such trays, however, are labor and time intensive in that the objects must be carefully positioned to avoid overlapping the objects and, further, that the objects must be turned over during a disinfection process to insure disinfection of surfaces that were originally placed in contact with the trays.

Accordingly, it would be advantageous to develop devices and processes that can aid in accessing all surfaces of objects during a disinfection process with minimal labor involved and minimal interruptions to the disinfection process.

SUMMARY OF THE INVENTION

Support structures, cabinets and methods are provided for disinfecting objects. The following description of various embodiments of support structure, cabinets and methods is not to be construed in any way as limiting the subject matter of the appended claims.

An embodiment of a method for disinfecting objects includes placing one or more objects into a cabinet and placing a disinfection device into the cabinet, wherein the disinfection device is configured to be independently operational from the cabinet and is further configured to project a germicide into an ambient of the disinfection device. The method further includes closing the cabinet with the disinfection device and the one or more objects inside the cabinet and remotely starting the disinfection device to disperse a germicide within the closed cabinet.

Another embodiment of a method of disinfecting objects includes placing one or more objects are placed into a second portion of a cabinet, which is adjacent a first portion of a cabinet having a disinfection device arranged therein or at least configured to accommodate a disinfection device. The method further include closing at least the first and second portions of the cabinet and remotely starting the disinfection device to disperse a germicide within at least the first and second portions of the cabinet. At some point during the process, the method includes segregating a third portion of the cabinet from the first portion of the cabinet using a germicide blocking partition and thereafter placing one or more objects into the third portion of the cabinet.

An embodiment of a cabinet includes an interior void of at least 10 ft$^3$, a door to enclose the cabinet and one or more support structures arranged within one or more areas of the cabinet adjacent the interior void. At least portions of the support structures facing the interior void are transparent and/or comprise through-holes. The support structures may include shelving, one or more baskets and/or one or more trays.

An embodiment of another cabinet includes a moveable partition for separating first and second portions of the cabinet, wherein the moveable partition is configured to block transmission of a germicide. In addition, the cabinet includes at least one door to allow access to at least the second portion of the cabinet and a sensor for detecting when the moveable partition is in position to separate the first and second portions of the cabinet.

An embodiment of a support structure includes a base comprising transparent materials and/or one or more through-holes, sidewalls shaped to match a peripheral contour of a medical device, and a weight sensor.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Devices and methods are provided that increase the versatility of operationally independent disinfection apparatuses, allow a majority if not all exterior sides of an object to be simultaneously disinfected and offer a manner to determine if an object has been deemed suitable for a particular disinfection system. More specifically, methods are provided which include placing one or more objects into a cabinet, placing a disinfection device into the cabinet, closing the cabinet with the disinfection device and the one or more objects inside the cabinet and remotely starting the disinfection device to disperse a germicide within the closed cabinet as set forth in FIG. 1. In addition, a method is provided in FIG. 7 for disinfection objects in a partitionable cabinet. Moreover, cabinets are provided which are specifically configured to enable such a processes as illustrated in FIGS. 2-6. Furthermore, support structures are provided which are configured to confirm an object placed thereon is suitable for a particular disinfection system, an example of which is set forth in FIGS. 8 and 9.

The objects considered for use in the methods, cabinets and support structures provided herein may include any configuration (i.e., shape, size, weight, material, construction, etc.) and may particularly depend on the configuration of the cabinet in which they are disinfected or the support structure upon which they are arranged. In some cases, objects which are relatively small and portable may be suitable for some of the cabinets described herein. In particular, some of the cabinets described herein include support structures, such as trays, shelving and/or baskets to hold objects during a disinfection cycle. In such cases, objects occupying less than approximately 1.0 $ft^3$ and, in some cases, objects occupying less than approximately 0.5 $ft^3$ may be particularly applicable for such processes In other cases, the cabinets described herein may be configured to disinfect larger objects, particularly those occupying more than approximately 1.0 $ft^3$. In any case, the methods, cabinets and support structures described herein may, in some cases, be used in hospital rooms. In such embodiments, objects which may be considered for use in the methods, cabinets and support structures provided herein may include medical items which are kept within a hospital. Non-medical items may be considered for use in the methods, cabinets and support structures provided herein as well, such as but not limited to pens, pads of paper, and pamphlets. In any case, objects of the same configuration or of different configurations may be considered for a given disinfection process.

As noted above, FIG. 1 outlines a method for disinfecting one or more objects in a cabinet. As shown, block 10 includes placing one or more objects into a cabinet. In some cases, the step of placing the one or more objects into the cabinet may include placing the one or more objects on one or more shelves arranged in the cabinet, placing the one or more objects on one or more trays arranged in the cabinet and/or placing the one or more objects in one or more baskets arranged within a cabinet as set forth in block 22. In some embodiments, the step of placing the one or more objects into the cabinet may additionally or alternatively include placing the one or more objects on one or more trays, on one or more shelves and/or in one or more baskets and then placing the one or more trays, the one or more shelves and/or the one or more baskets in the cabinet as respectively set forth in blocks 24 and 25.

In any case, the shelving, basket/s and/or tray/s may be arranged at any location in the cabinet. In some embodiments, one or more shelves, one or more baskets and/or one or more trays may be attached and/or extend from sidewalls of the cabinet and/or door/s of the cabinet. In addition or alternatively, one or more baskets may be hung from the ceiling of the cabinet. Furthermore, one or more baskets and/or one or more trays may be arranged on a floor of the cabinet and/or may be arranged on a shelf in the cabinet. In any case, the shelving, the basket/s and/or the tray/s considered for the methods, cabinets and support structures provided herein include portions which are transparent and/or include through holes. In some embodiments, the size of the through holes in the shelving, basket/s and/or tray/s may be relatively large (i.e., the through holes may occupy more space than the framework surrounding the through holes, such as commonly found in wired racks or polymer frameworks having a configuration similar to a wire rack. In some cases, one or more of the shelves, basket/s and/or tray/s may be made of entirely transparent material/s.

The term "cabinet" as used herein refers to an article for enclosing and holding one or more items, wherein the article has a door for receiving the one or more items and for closing the cabinet, and wherein the article may be either moved wholly or moved by dismantling at least some of the framework of the cabinet and reconstructing the cabinet from the dismantled framework at a different location. The term is distinct from areas of a building that are primarily bordered by fixed constructs of a building, such as by drywall or concrete, in that those constructs cannot be dismantled and readily reused to construct a wall. In particular, the term "cabinet" as used herein does not refer to rooms in a building, hallways, bathrooms, or closets having fixed sidewalls composed of materials commonly used to define interior spaces within a building such as but not limited to drywall or concrete. In contrast, the term is inclusive to reconstructable and/or moveable articles. For example, the term is inclusive to wall mounted articles, including but not limited to backless boxes which utilize a wall of a room to form an enclosure for the cabinet. In particular, wall mounted cabinets may be either moved wholly or moved by dismantling the cabinet and reconstructing the cabinet from the dismantled framework at a different location. Furthermore, the term "cabinet" as used herein encompasses free-standing reconstructable or moveable enclosures. Moreover, the term encompasses reconstructable or moveable articles which utilize the floor and/or the ceiling to form the enclosure for the cabinet. As such, articles which do not include a floor and/or a ceiling but which form an enclosure with a floor or ceiling of a building may be considered herein a cabinet when the article is arranged in such a manner.

Figure 1:
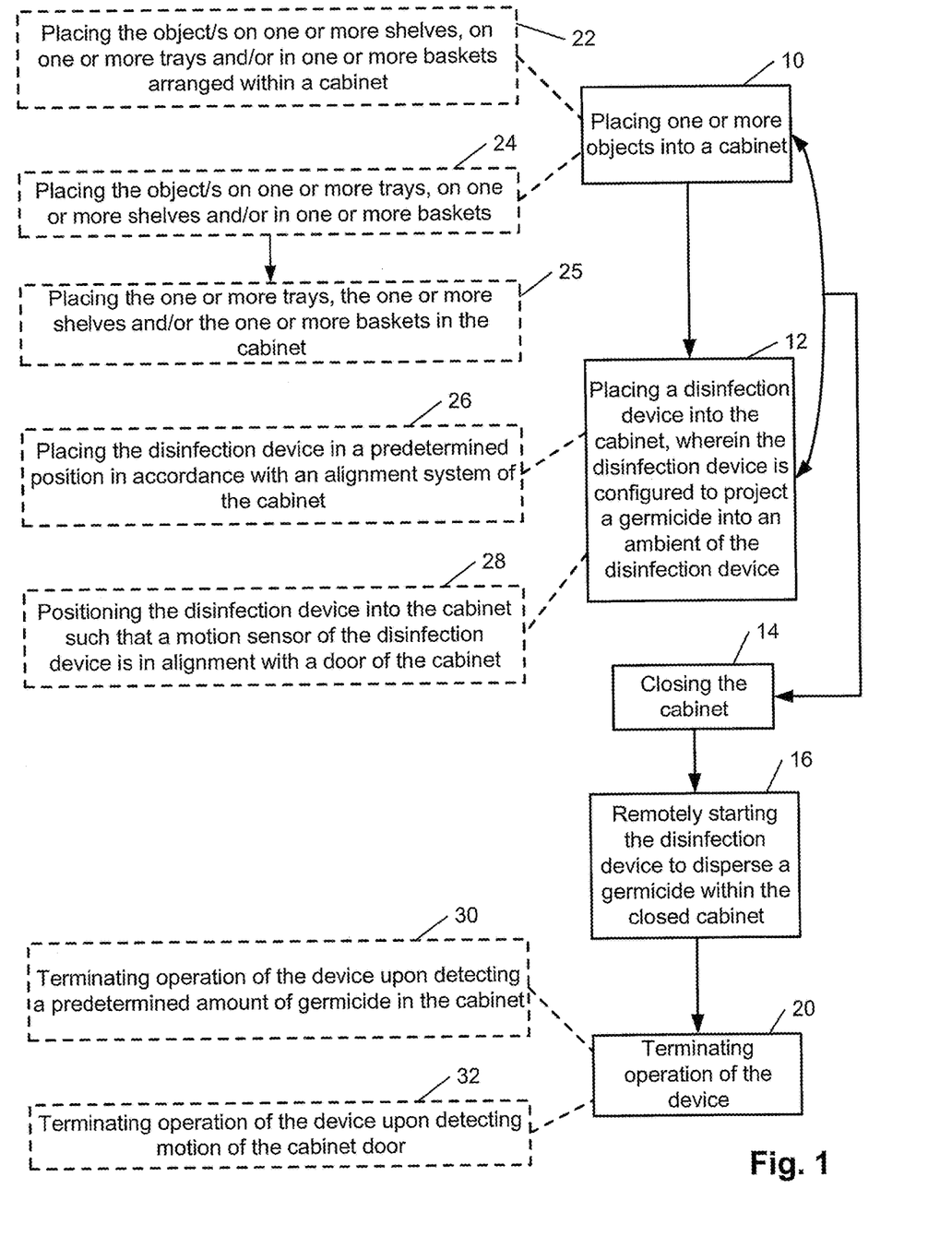
FIG. 1 illustrates an example flowchart of a method for disinfecting one or more objects in a cabinet.

As shown in block 12, the method outlined in FIG. 1 further includes placing a disinfection device into the cabinet. The doubled arrow line between blocks 10 and 12 indicates that either process may be conducted prior to the other or they may be performed at substantially the same time. In any case, the method continues to block 14 to close the cabinet and further to block 16 to remotely start the disinfection device to disperse a germicide within the closed cabinet. In some cases, the disinfection device may be configured to be independently operational from the cabinet. Alternatively stated, the disinfection device placed into the cabinet may be configured to be operational independent from the cabinet. More specifically, the disinfection devices considered herein may be free-standing devices having their own power source and/or a power cord for accessing their own power. Thus, the functional features of the disinfection device need not be coupled to the cabinet for the disinfection device to operate.

Such a configuration of a disinfection device does not necessarily mandate that the disinfection device be operationally independent from the cabinet during a disinfection cycle, but rather that it merely has the configuration to do so. For instance, as set forth in more detail below, the cabinets described herein may, in some embodiments, include a power outlet arranged along an interior surface for receiving a power plug and further a power cord coupled to the power outlet and extending out from an exterior surface of the cabinet. Such a configuration may be useful for supplying power to the disinfection device through the cabinet. In particular, a power plug of a disinfection device may be plugged into the power outlet of the cabinet and the power cord of the cabinet may be plugged into a power outlet coupled to a mains power supply of a building. In this manner, the power cord of the disinfection device need not be routed exterior to the cabinet. In other embodiments, however, the power cord of the disinfection device may be routed exterior to the cabinet, such as under a sidewall of the cabinet or through a hole along a sidewall of the cabinet, to directly connect the disinfection device to a power outlet coupled to a mains power supply of a building.

The disinfection devices considered herein may be any device configured to generate a dispersible germicide. In particular, the disinfection devices considered herein may be any device or apparatus configured to generate a germicide in form of a liquid, a vapor, a gas, a plasma or germicidal light. In some cases, a disinfection device may be configured to generate more than one type of germicide. As used herein, the term "germicide" refers to an agent for deactivating or killing microorganisms, particularly disease carrying and/or disease producing microorganisms (a.k.a, germs). The term "kill," as used herein, means to cause the death of an organism. In contrast, the term "deactivate," as used herein, means to render an organism unable to reproduce without killing. As such, a germicide which is configured to deactivate a microorganism, as used herein, refers to an agent which renders a microorganism unable to reproduce but leaves the organism alive. Furthermore, the term "disinfection device" as used herein refers to a collection of one or more components used to generate and disperse a germicide. In some embodiments, a disinfection device may include components in addition to the component/s used to generate the germicide to effect the dispersal of the germicide from the generation component/s. In any case, the disinfection devices described herein may include any number of germicidal sources, depending on the design specifications of the disinfection device.

In some cases, a germicidal source of the disinfection devices described herein may be configured to generate a liquid, vapor, gaseous or plasma germicide that is molecularly configured to deactivate and/or kill microorganisms. As used herein, the phrase "molecularly configured" refers to the elemental composition of a substance (i.e., the number and type of atoms making up a substance) to impart the function stated after the phrase. In some embodiments, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms. This is in contrast to liquid, vapor, gaseous or plasma germicides which impart their deactivation and/or killing functionality by the manner in which they are used. For example, boiling water and steam are often effective sterilizing agents due to the temperature at which they are employed rather than their molecular composition. An example of a gaseous germicide which deactivates or kills microorganisms by the manner in which it is used is air at a very high temperature. Furthermore, the germicidal effectiveness of some plasma germicides is primarily due to the presence and activity of charged particles making up the plasma rather than the molecular composition of the charged particles.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that although germicidal sources which are configured to generate a liquid, vapor, gaseous or plasma germicide that is molecularly configured to deactivate or kill microorganisms are discussed in detail above, the disinfection devices considered herein may, in some embodiments, include a germicidal source configured to generate a liquid, vapor, gaseous or plasma germicide which imparts its deactivation or killing functionality by the manner in which it is used, such as via boiling water, steam or heated air. In any case, examples of disinfection devices which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide.

As noted above, a germicidal source of the disinfection devices described herein may, in some embodiments, be a source configured to generate germicidal light. The term "germicidal light" refers to light which is capable of deactivating or killing microorganisms, particularly disease carrying and/or disease producing microorganisms (a.k.a., germs). Ranges of light which are known to be germicidal include ultraviolet light between approximately 200 nm and approximately 320 nm, particularly 220 nm and between 260 nm and 265 nm, and visible violet-blue light (also known as high-intensity narrow-spectrum (HINS) light) between approximately 400 nm and approximately 470 nm, particularly 405 nm. In some embodiments, a germicidal light source may generate ranges of light which are not germicidal such as but not limited to visible light greater than approximately 500 nm, but such capability will not deter from the reference of the light sources being germicidal. Furthermore, a light source or lamp may, in some cases, be characterized in the type of light it generates, but such characterization need not limit the light source or lamp to generating only that type of light. For example, an ultraviolet lamp is one which generates ultraviolet light but it may produce light of other wavelengths. In any case, the germicidal light sources considered for the disinfection devices described herein may be of any size and shape, depending on the design specifications of the disinfection devices. The terms "germicidal light source" and "germicidal lamp" are used interchangeably herein and refer to a collection of one or more components used to generate and disperse germicidal light.

Examples of germicidal light sources which may be configured to generate ultraviolet light and/or HINS light include discharge lamps, light emitting diode (LED) solid state devices, and excimer lasers. HINTS lamps are generally constructed of LEDs. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the germicidal sources described herein include gas-discharge lamps as well as surface-discharge lamps. Discharge lamps may be further characterized by the type of gas/es employed and the pressure at which they are operated. The discharge lamps which may be considered for the germicidal sources described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the germicidal sources described herein may include those which generate continuous light and those which generate light in short durations, the latter of which are often referred to as flashtubes or flashlamps. Flashtubes or flashlamps that are used to supply recurrent pulses of light are often referred to as pulsed light sources.

A commonly used gas-discharge lamp used to produce continuous light is a mercury-vapor lamp, which may be considered for some of the disinfection devices described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the disinfection devices described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the disinfection devices described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the disinfection devices described herein to include such lamps. Rather, the aforementioned descriptions and comparisons are merely provided to offer factors which one skilled in the art may contemplate when selecting a germicidal light source for disinfection devices described herein.

As noted above, in some cases, the germicidal light source may be an excimer laser and, thus, the germicidal light used to disinfect objects in the cabinet may be a narrow beam of light. In such cases, a disinfection device comprising the laser may be configured to move the laser such that multiple or all locations in the cabinet are disinfected. Alternatively, a disinfection device may be configured to distribute germicidal light into an ambient of a room in a spacious manner such that at least the portions of an object in the vicinity of the disinfection device may be simultaneously disinfected. The disinfection device may be of any shape, size, or configuration in which to achieve such an objective.

In some cases, it may be advantageous for the methods and cabinets described herein to utilize a room disinfection device. More specifically, the methods and cabinets described herein may, in some cases, utilize disinfection devices with configurations to facilitate room disinfection. As used herein, the term "room disinfection device" refers to a device configured to disinfect a space which is suitable for human occupancy so as to deactivate, destroy or prevent the growth of disease-carrying microorganisms in the area. The phrase "a space which is suitable for human occupancy" as used herein refers to a space in which an adult human being of average size may comfortably occupy for at least a period of time to eat, sleep, work, lounge, partake in an activity, or complete a task therein. In some cases, spaces suitable for human occupancy may be bounded and include a door for entering and exiting the room. In other cases, a space suitable for human occupancy may be an area with indeterminate boundaries. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations.

In general, a room disinfection device includes configurations to distribute an effective amount of germicide in a spacious manner to an ambient of a room in which the device is arranged to maximize the number of surfaces and objects disinfected in the room. The device may be of any shape, size, or configuration in which to achieve such an objective. An example configuration of a room disinfection device which may be particularly considered for the disinfection devices discussed herein is for the germicidal source to be arranged within the device to distribute a germicide approximately 360° around the source. In such cases, the room disinfection device may be void of a component sufficient to block the germicide approximately 360° around the device such that germicide emitted from the germicidal source substantially encircles the device. Another configuration of a room disinfection device is to be automated to move through a room or area while the germicidal source is projecting germicide into an ambient of the room or area. For instance, some room disinfection devices include motorized wheels and processor-executable program instructions for activating the motorized wheels in accordance with a predetermined route and/or in response to sensors to maneuver around obstacles in the room or area while the germicidal source is emitting germicide/s. It is noted that although a room disinfection device may include such a configuration, such a movement feature would not be used in conjunction with the methods and cabinets disclosed herein.

Another common feature of room disinfection devices which may be optionally included in the disinfection devices considered for the methods described herein is to be configured to direct germicidal light to a region approximately 2 feet and approximately 4 feet from a floor of a room in which the apparatus is arranged. In particular, the region between approximately 2 feet and approximately 4 feet from a floor of a room is considered a "high touch" region of a room since objects of frequent use are generally placed in such a region. Examples of configurations which offer such light direction are disclosed in U.S. patent application Ser. No. 13/706,926 filed Dec. 6, 2012 and Ser. No. 13/708,208 filed Dec. 7, 2012 and International Patent Application No. PCT/US2014/059698 filed Oct. 8, 2014, all of which are incorporated herein by reference as if set forth fully herein. Other features specific to room disinfection devices are disclosed in such documents as well. For example, other features of room disinfection devices include wheels and/or a handle to affect portability for the devices. In addition, many room disinfection devices include configurations for remotely starting the devices such that individuals need not be present in the room when operation of the device commences.

Figure 2:
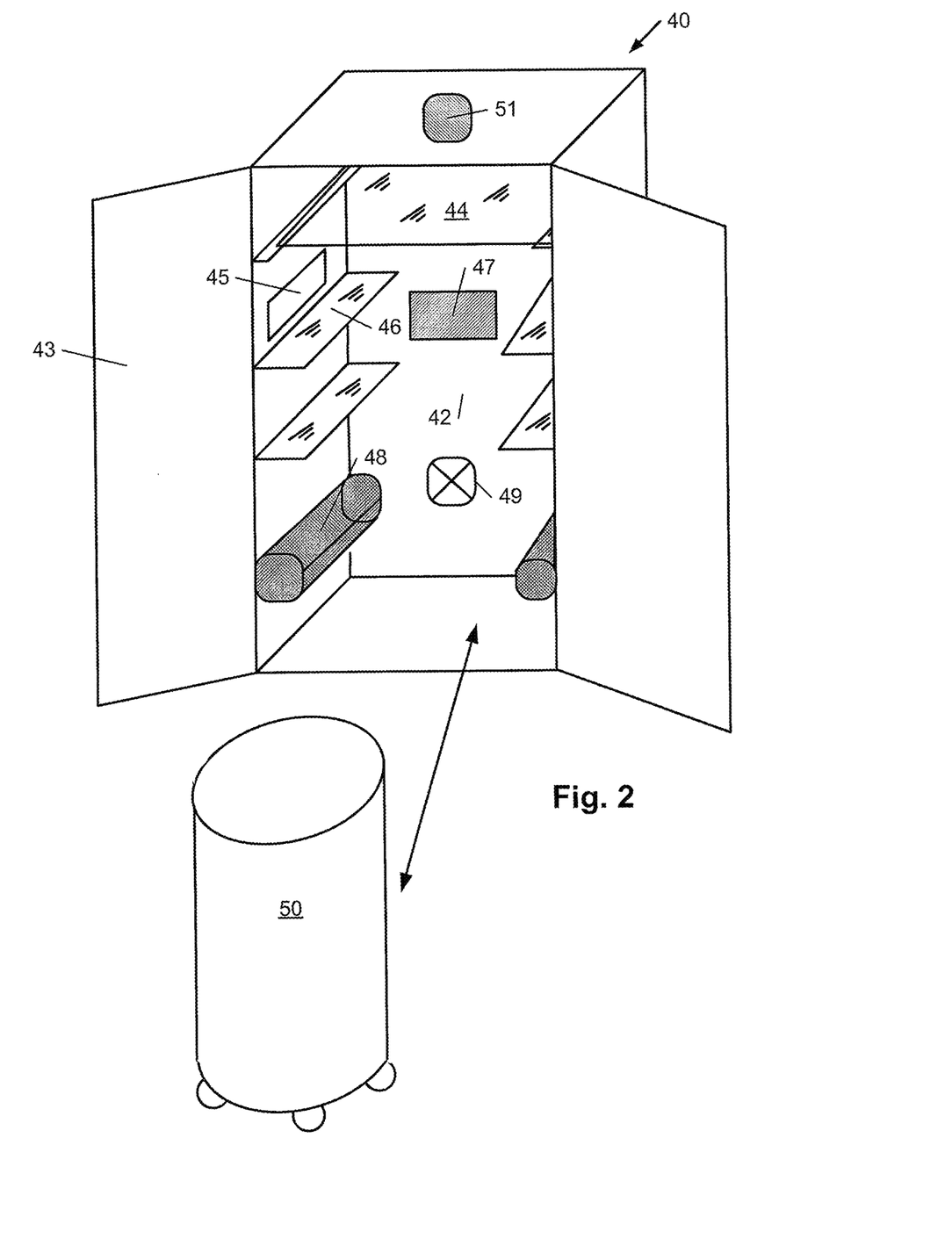
FIG. 2 illustrates a perspective view of an example cabinet for disinfecting one or more objects.

Another feature of a room disinfection device which may be included in the disinfection devices considered for the methods described herein is to include configurations to distribute an effective amount of germicide to achieve at least a 2-log reduction in bacterial contamination on surfaces within a room or area that are greater than 1 meter or even 2 or 3 meters from the germicidal source. Configurations used to generate such an effect generally depend on the configuration of the germicidal source, particularly the size of the germicidal source, the intensity and/or frequency at which the germicide is dispersed and the orientation of the germicidal source in the apparatus. In general, the germicidal sources considered herein may, in some embodiments, be any shape, size, orientation or configuration and may be conducted at parameters to achieve a desired reduction in bacterial contamination on surfaces within a room or area that are greater than 1 meter or even 2 or 3 meters from the apparatus. An example of an orientation of a germicidal source which may aid in achieving such an effect is that the germicidal source may be vertically arranged (e.g., the germicidal source may be arranged lengthwise substantially perpendicular to a horizontal plane of the support structure) to aid in distributing the germicide greater distances within a room or area. Moreover, power fluxes of at least 1.0 $W/m^2$ may be generally used to achieve at least a 2-log reduction in bacterial contamination on surfaces within a room or area that are greater than 1 meter from the germicidal source.

In some cases, room disinfection devices may utilize configurations of other components in the device (i.e., other than the configurations of the germicidal source) to aid in achieving a desired reduction in bacterial contamination on surfaces within a room or area that are greater than 1 meter or even 2 or 3 meters from the germicidal source. For example, room disinfection devices may, in some embodiments, include an actuator coupled to the germicidal source and processor-executable program instructions for activating the actuator to move the germicidal source while the germicidal source is projecting germicide into an ambient of a room or area to aid in the distribution of germicide in a room or area. More specifically, the germicidal source may be moved in vertical, horizontal and/or diagonal directions via the actuator while the germicidal source is projecting germicide into an ambient of a room or area. Such a configuration may, in some embodiments, be included in the disinfection devices considered for the methods described herein and activated during a disinfection cycle in a cabinet. In particular, moving the germicidal source within a cabinet may aid in distributing the germicide among the different support structures in the cabinet.

Another component which is often included in room disinfection devices which may be included in the disinfection devices considered for the methods described herein is a movement detection sensor and/or a room/area occupancy sensor, such as a motion sensor, a thermal sensor, a Doppler sensor, or a photo recognition sensor. In particular, the disinfection devices considered herein may include program instructions to inhibit or terminate activation of a power supply circuit to the germicidal source as denoted in block 20 of FIG. 1, such as upon detecting movement and/or occupancy in the area/room in which the apparatus is arranged. In cases in which the cabinet in which the disinfection device is positioned for the methods described herein is configured to move objects therein, the disinfection device may include a switch to activate and deactivate an occupancy sensor. In other embodiments, the sensor/s and the program instructions may be used when the disinfection device is placed in a cabinet for disinfecting objects. In particular, the method disclosed herein may include positioning the room disinfection device in the cabinet such that a motion sensor comprising the room disinfection device is in alignment with a door of the cabinet as set forth in block 28 of FIG. 1. In this manner, if the door to the cabinet is opened during operation of the disinfection device, power supply to the disinfection device will be terminated as set forth in block 32 of FIG. 1.

In any case, cabinets are provided herein which are specifically configured to enable simultaneous disinfection of a majority if not all surfaces of one or more objects. As described in more detail above, the cabinets include shelving, one or more baskets and/or one or more trays, at least portions of which are transparent and/or comprise through-holes. As further described above, the shelving, basket/s and/or tray/s may be arranged along the sidewalls, door/s, ceiling or floor of the cabinet. In addition to such support structures, the cabinets include a void of sufficient size to accommodate a disinfection device. In general, disinfection devices come in various sizes and, thus, the size of the void may vary, depending on the design of the cabinet. Some disinfection devices, particularly room disinfection devices, are relatively large units (i.e., 10 $ft^3$ or greater) and, thus, the void may, in some cases, be of sufficient size to accommodate such a device. In any case, the shelving, basket/s and/or tray/s of the cabinet are adjacent to the void and, in some cases, circumvent the void. In some embodiments, the void may centered in the cabinet. In any case, portions of the support structures facing the void may be transparent and/or may include through-holes such that objects placed on the support structures may be exposed to a germicide projected from a disinfection device occupying the void. In some embodiments, the cabinet and/or the one or more support structures may include an automated means for moving one or more objects placed on or in the one or more support structures, such as a vibrator for example. For example, the cabinet may include vibrating wire racks.

An example of a cabinet having such features is illustrated in FIG. 2. In particular, FIG. 2 illustrates cabinet 40 having interior void 42 of at least 10 $ft^3$, tray 44, shelving 46 and baskets 48 adjacent the interior void, wherein at least portions of the tray, shelving and baskets facing the interior void are transparent and/or comprise through-holes. In addition, cabinet 40 includes door 43. In some cases, cabinet 40 may include loading port 45 adjacent to tray 44, shelving 46 and/or baskets 48 as an additional or alternative manner in which to load one or more objects into the cabinet. As set forth above, interior void 42 is of sufficient size to accommodate disinfection device 50.

In addition or alternatively, the cabinets considered herein may, in some embodiments, have alignment markers and/or an alignment system such that a disinfection device may be placed in a predetermined position within the void of the cabinet as denoted in block 26 of FIG. 1. In some cases, the alignment markers and/or alignment system may be configured such that the germicidal source of the disinfection device is a specified distance from the support structures upon which objects will be placed in the cabinet. In particular, some types of germicidal sources generate intense amounts of heat and, thus, pose a risk of causing items too close to the source of getting too hot to touch after a disinfection process, melt or catch fire. An exemplary range of distances that the alignment markers and/or alignment system may be based on may between approximately 3 inches and approximately 12 inches, but shorter and longer distances may be employed.

Various other configurations may be considered for the cabinets as well. For example, in some cases, the cabinets may be absent a floor or, alternatively, include a floor with a tapered lip such that in either case a disinfection device may be wheeled into the cabinet. In the latter of such embodiments, the cabinet may include a door extending in proximity to the tapered lip. In some cases, a cabinet may include a single door by which to load objects and a disinfection device into the cabinet. In other embodiments, cabinet may include multiple doors. For instance, a cabinet may include a first door for primarily loading a disinfection device into the cabinet and a second door for primarily loading objects into the cabinet. In other cases, cabinets that have multiple doors may not have loading designations for their doors. In any case, the cabinets considered herein may, in some embodiments, include a power outlet along its interior for receiving a power plug of a disinfection device. The power outlet may be coupled to a power cord extending out from an exterior surface of the cabinet such that the disinfection device may be coupled to a mains power supply of a building when arranged in the cabinet. Alternatively, a cabinet may include an opening near its lower end such that a power cord of a disinfection device may be routed therethrough to a power outlet along a wall of a room in which the cabinet is arranged. In yet other cases, a cabinet may be void of such provisions, particularly if the cabinet is specifically designed to accommodate a particular disinfection device that is powered by its own battery.

In some embodiments, the cabinets provided herein may be free-standing units. In other cases, the cabinets may be mounted to a wall. In either case, the cabinets may extend to a floor of a room in which it is arranged, but in other embodiments, they may not. In some embodiments, the sidewalls and doors of the cabinets may be sealed to prevent a germicide generated from a disinfection device therein from leaking out of the cabinet. In other cases, the cabinets may not be sealed. In some embodiments, the cabinets may include a highly reflective material along one or more of its interior surfaces, including the sidewalls, ceiling and/or floor of the cabinet, if applicable. In some cases, the highly reflective materials may be those highly reflective to ultraviolet light and/or visible violet-blue light. In particular, it may be advantageous for at least a portion of the cabinets to include a material which exhibits greater than 50% reflectance to ultraviolet light and/or visible violet-blue light, or more specifically, greater than 85% reflectance to ultraviolet light and/or visible violet-blue light. Examples of reflective materials which may be employed include but are not limited to metalized nylon, Teflon, aluminum, reflective paint, biaxially-oriented polyethylene terephthalate (boPET) (e.g., Mylar), and GORE® DRP® Diffuse Reflector Material available from W. L. Gore & Associates, Inc. In addition or alternative to being highly reflective, the cabinets may include a variety of other material characteristics along its interior surface, such as but not limited to being antimicrobial.

In some cases, the cabinets described herein may include one or more fans for cooling the interior of the cabinets and/or dispersing a liquid or gas germicide generated by a disinfection device arranged in the cabinet, such as shown by reference number 49 in FIG. 2. The one or more fans may be arranged interior to the cabinet and/or may be arranged within the sidewalls or ceiling of the cabinet. In embodiments having the latter arrangements, the fans may be configured to drawn air in or out of the cabinet. In some cases, the cabinet may include an ozone reducing device disposed within a wall or ceiling of the cabinet extending between an interior of the cabinet to an exterior of the cabinet such as shown by reference number 51 in FIG. 2. In particular, ozone may, in some cases, be created as a byproduct from the use of germicidal light source, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated. Examples of ozone reducing devices which may be included in the cabinets described herein include but are not limited to a carbon filter or a device which produces free radicals catalysts that covert ozone to diatomic oxygen.

In some embodiments, the cabinets described herein may include one or more germicide dose sensor/s for detecting the amount of germicide dispersed in the cabinet. In some cases, the germicide dose sensor/s may be configured to affect the operation of a disinfection device arranged in the cabinet. In particular, the cabinet and/or the disinfection device may include a storage medium with processor executable program instructions to shut off the disinfection device when a signal is received from the germicide dose sensor/s indicating that a predetermined dose of germicide is detected within the cabinet as denoted in block 30 of FIG. 1. In additional or alternative embodiments, the cabinets described herein may include a humidity and/or temperature control system, such as shown by reference number 47 in FIG. 2. In particular, the cabinets described herein may include dehumidifiers and/or cooling devices to control the humidity and temperature of the interior of the cabinet. In particular, controlling the humidity and/or temperature of an environment sometimes improves the germicidal efficacy of a germicidal source and, thus, may be used to optimize disinfection cycle time.

In some embodiments, the cabinets provided herein may include a user interface. The user interface may be used for setting disinfection process parameters and/or communicating conditions of various systems comprising the cabinet. For example, in some cases, the cabinet may include a system (e.g., a machine vision system) to ensure objects on the support structures of the cabinet are not touching each other. In addition or alternatively, the cabinet may include a safety mechanism ensuring door/s of the cabinet are closed. In some cases, the cabinet may include an identification system of objects placed in the cabinet to ensure objects placed in the cabinet are those that have been deemed suitable for a particular disinfection system. In some embodiments, an identification system for objects may include scanning identification system (such as a barcode reader or an RF receiver) for identifying objects placed in the cabinet having an identification tag. In some cases, an identification system of a cabinet may be augmented with a weight sensor in one or more of the support structures upon which objects are placed for a disinfection process. In particular, a weight sensor may be used to verify whether the weight of an object placed on the support structure is in an appropriate range for what it has been identified as via the scanning identification system. In any case, the user interface may be configured to project audio commands (i.e., have a speaker and program instructions for sending signals for an audio command to be broadcasted) and/or display visual commands (i.e., include as screen and program instructions for displaying text or pictorial information thereon) for setting disinfection process parameters and/or communicating conditions of various systems comprising the cabinet.

Figure 3:
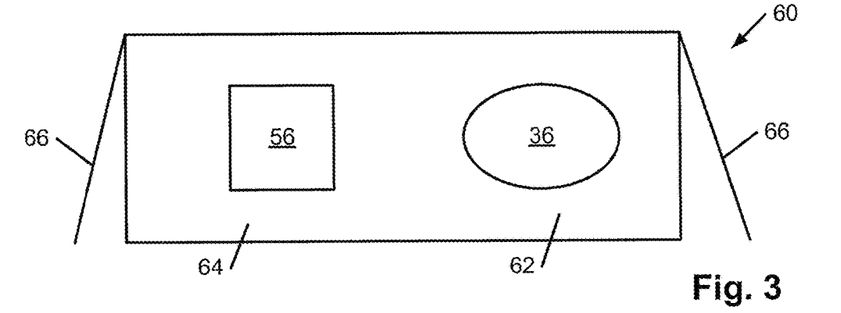
FIG. 3 illustrates a schematic top view of another example cabinet for disinfecting one or more objects.

As shown in FIG. 2 and described above, the configuration of cabinet 40 is specific to having void 42 substantially central to cabinet 40 with tray 44, shelves 46 and baskets 48 arranged around void 42. The cabinets described herein, however, are not necessarily so limited. In particular, cabinets considered herein may have off-center void regions for accommodating a disinfection device. FIG. 3 illustrates a top view schematic drawing of cabinet 60 having disinfection device 36 disposed off-center in the cabinet, particularly in portion 62 of the cabinet opposing portion 64 having one or more objects 56 disposed therein. In general, one or more objects 56 may include object/s of any configuration (i.e., shape, size, weight, material, construction, etc.). In some cases, object/s 56 may be disposed on tray/s, shelving and/or basket/s arranged in portion 64. In some of such cases, the tray/s, shelving and/or basket/s may be arranged along interior surfaces of portion 64 such as described for the tray/s, shelving and/or baskets of cabinet 40 in FIG. 2. In addition or alternatively, tray/s, shelving and/or basket/s may be supported by a free-standing rack arranged in portion 64 of cabinet 60. In some cases, the free-standing rack may include wheels or some other displacement mechanism to affect mobility and portability of the rack. In such embodiments, the rack may be preloaded with one or more objects 56 prior to being placed in portion 64 of cabinet 60. In other cases, the rack may not include a displacement mechanism and, in some embodiments, the rack may be secured within cabinet 60.

In alternative embodiments, one or more objects 56 may be placed on the floor of cabinet 60 or the floor upon which the cabinet is arranged. In such cases, the one or more objects 56 may not be placed on a specific support structure within cabinet 60. In some of such embodiments, one or more objects 56 may include an object with wheels or some other displacement mechanism to affect mobility and portability of the object/s. Alternatively, one or more objects 56 may be void of displacement mechanisms. In any case, to accommodate a rack or free standing objects within portion 64, portion 64 may include a void space sufficient to receive the rack or free-standing object. The void space may be on the order of greater than approximately 1.0 ft$^3$, greater than approximately 5.0 ft$^3$ and, in some cases, greater than approximately 10.0 ft$^3$.

As noted above in reference to FIG. 2, some of the cabinets disclosed herein may include a void space greater than approximately 10.0 ft$^3$ to accommodate a disinfection device generally configured for room disinfection. In some embodiments, portion 62 may include such a void space. In other cases, however, disinfection device 36 need not be so large and, thus, portion 62 may be smaller than 10.0 ft$^3$. In general, disinfection device 36 may include any device configured to generate a dispersible germicide. Although disinfection device 36 may be configured to be independently operational from cabinet 60 and/or may be configured for room disinfection such as described above for disinfection device 50, disinfection device 36 need not be so limited. In particular, disinfection device 36 may, in some embodiments, be operationally dependent on cabinet 60, specifically that the power used to operate the device is drawn through the cabinet. In addition or alternatively, disinfection device 36 need not include all or any of the features described above that are generally associated with room disinfection devices.

As shown in FIG. 3, cabinet 60 may include doors 66 for allowing separate access to portions 62 and 64. Such a configuration may ease loading of one or more objects 56 and disinfection device 36 into the cabinet. In alternative embodiments, however, cabinet 60 may include a single door. In addition or alternatively, cabinet 60 may include closable loading ports along its exterior surface aligned with support structures in portion 64 when cabinet 60 includes such support structures. In any case, the door/s and/or loading port/s may be arranged along any portion of the cabinet and, thus, the positions of the door/s and loading port/s should not be limited to be on opposing ends of the cabinet as shown in FIG. 3. Furthermore, the door/s and loading port/s of the cabinet may be hinged doors, sliding doors, or retractable doors and, thus, should not be limited to the hinged doors shown in FIG. 3.

Figure 4:
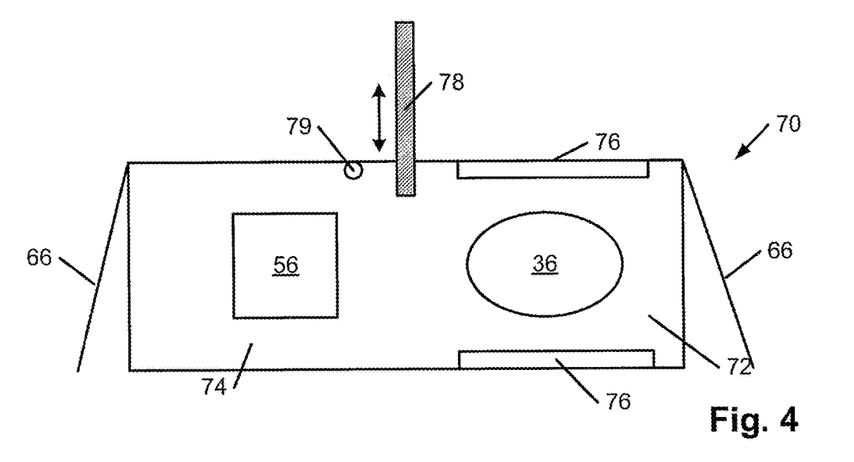
FIGS. 4-6 illustrate schematic top views of different example cabinets having partitionable chambers for disinfection one or more objects.

Although portion 62 of cabinet 60 is shown absent of object/s therein, use of the cabinet should not be so limited. In particular, one or more objects may be placed in portion 62 as long as they do not interfere with the arrangement of disinfection device 36. FIG. 4 illustrates cabinet 70 having support structures 76 (i.e., tray/s, shelving and/or baskets) arranged adjacent to disinfection device 36 in portion 72 of the cabinet. In addition, cabinet 70 includes portion 74 having one or more objects 56 placed therein as similarly described for one or more objects 56 in portion 64 of cabinet 60 in FIG. 3. To increase efficiency, it may be advantageous in some cases to successively load one or more objects into portions 72 and 74 of cabinet 70. In such embodiments, it may be advantage to partition portion 74 from portion 72 such that the one or more objects placed in portion 74 may be disinfected from a germicide projected from disinfection device 36 while one or more objects 56 are placed into portion 74. As such, cabinet 70 include moveable partition 78 to separate portions 72 and 74 of cabinet 70. Moveable partition 78 is configured to block transmission of a germicide generated by disinfection apparatus 36. In embodiments in which the germicide is a liquid, gas, mist or plasma, any non-pervious material may be used for partition 78, such as glass, plastics, metals, or wood. In some cases, at least the side of partition 78 facing disinfection device 36 may include a material which is resistant to chemical erosion. In cases in which the germicide generated by disinfection apparatus 36 is germicidal light, at least the side of partition 36 facing disinfection device 36 may include a material which attenuates the germicidal light. Further to having partition 78, cabinet 70 may include sensor 79 for detecting when partition 78 is in position to separate portions 72 and 74 of the cabinet.

Figure 5:
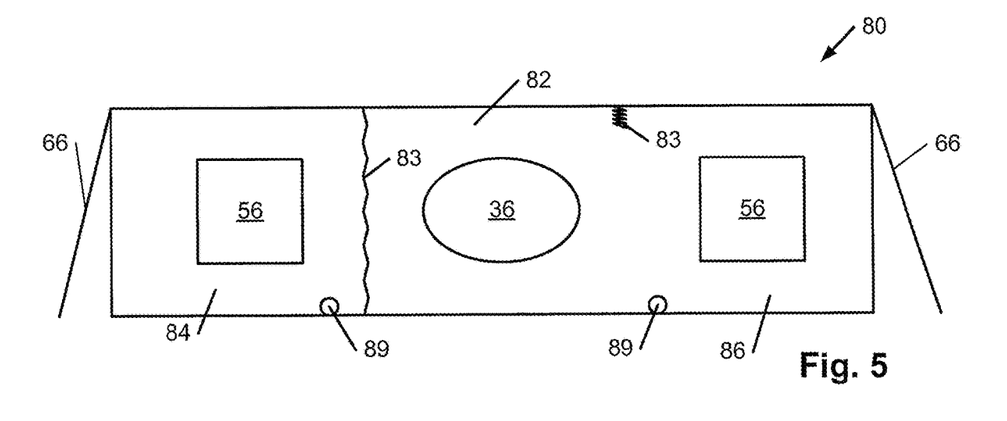
Figure 6:
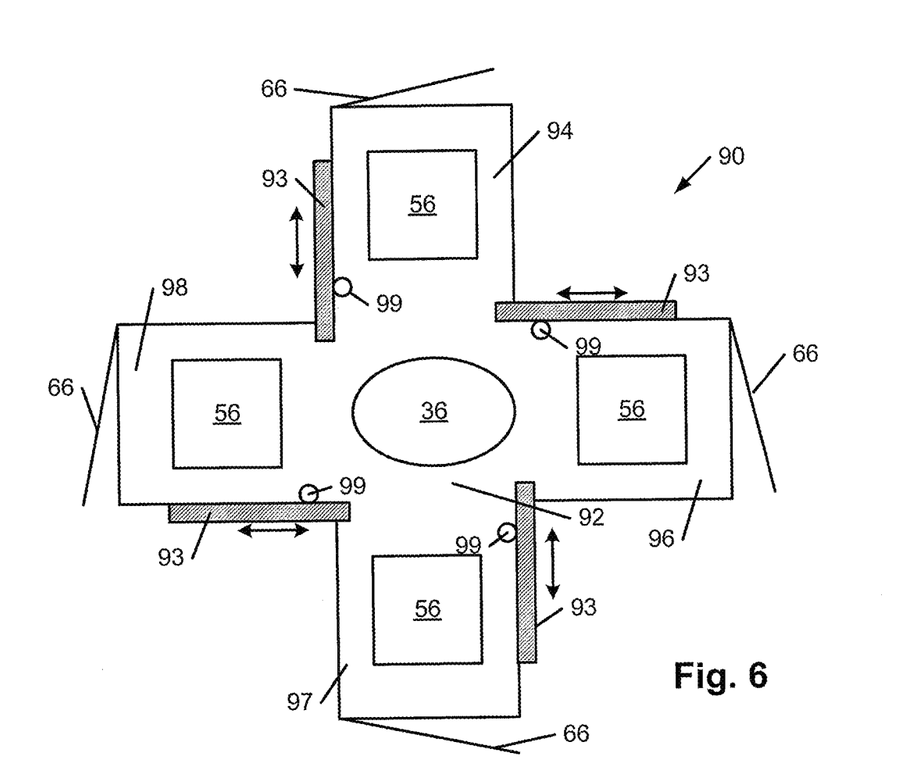

Cabinets with more than one partition are illustrated in FIGS. 5 and 6. In particular, FIG. 5 illustrates cabinet 80 having moveable partitions 83 respectively separating portions 84 and 86 from portion 82 and sensors 89 for detecting when partitions 83 are in position to respectively separate portions 72 and 74 of the cabinet. In addition, FIG. 6 illustrates cabinet 90 having moveable partitions 93 respectively separating portions 94, 96, 97, and 98 from portion 92. Furthermore, FIG. 6 illustrates cabinet 90 having sensors 99 for detecting when partitions 93 are in position to respectively separate portions 94, 96, 97, and 98 of the cabinet. As shown, portions 82 and 92 accommodate disinfection device 36 and each of portions 84, 86, 94, 96, 97 and 98 accommodate one or more objects 56. Moreover, each of cabinets 80 and 90 include doors 66 for respectively accessing portions 84, 86, 94, 96, 97 and 98. Partitions 83 differ from partition 78 of cabinet 70 and partitions 93 of cabinet 90 in that they are retractable within the cabinet. The variation of the partition is not specific to the configuration of cabinet 80 nor are partitions 78 and 93 specific to cabinets 70 and 90. Any type of moveable partition may be employed in the cabinets described herein, including but not limited to those shown in FIGS. 4-6 but as well as those which move vertical from or through the ceiling of the cabinets.

Figure 7:
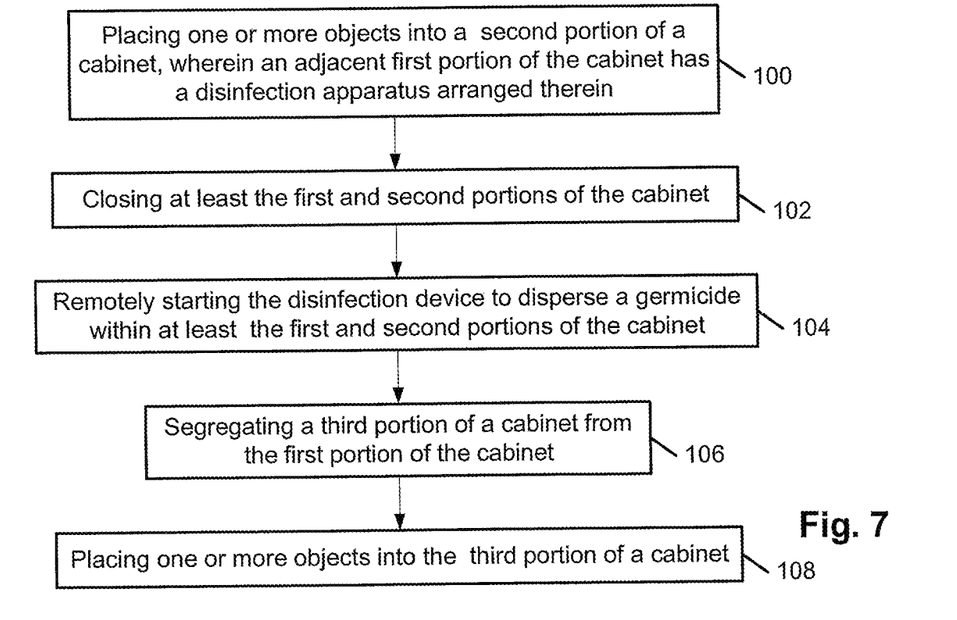
FIG. 7 illustrates an example flowchart of a method for disinfecting one or more objects in a cabinet having partitionable chambers.

A method of disinfecting objects within cabinets having partitionable portions or chambers, such as shown and described above in reference to FIGS. 5 and 6, is shown in FIG. 7. In particular, FIG. 7 includes block 100 in which one or more objects are placed into a second portion of a cabinet, which is adjacent a first portion of a cabinet having a disinfection device arranged therein or at least configured to accommodate a disinfection device. In the latter of such embodiments, a disinfection device may be placed within the first portion of the cabinet during or after the one or more objects are placed into the second portion of the cabinet. Thereafter, the method continues with closing at least the first and second portions of the cabinet as denoted in block 102. Subsequently in block 104, the disinfection device is remotely started to disperse a germicide within at least the first and second portions of the cabinet. At some point before, during or after any of the processes denoted in blocks 100, 102 and 104, a third portion of the cabinet is segregated from the first portion of the cabinet designated to house the disinfection device using a germicide blocking partition, such as described above in reference to FIGS. 4-6. After such segregation, one or more objects are placed into the third portion of the cabinet as denoted in block 108 of FIG. 7. Due to the germicide blocking partition, the process of block 108 may, in some cases, be performed while the disinfection device is generating and projecting a germicide into the first and second portions of the cabinet. Such a method may be similarly facilitated for other chambers of the cabinet such that there may be a succession of simultaneous loading the cabinet with object/s and disinfecting object/s within the cabinet among the different chambers.

Figure 8:
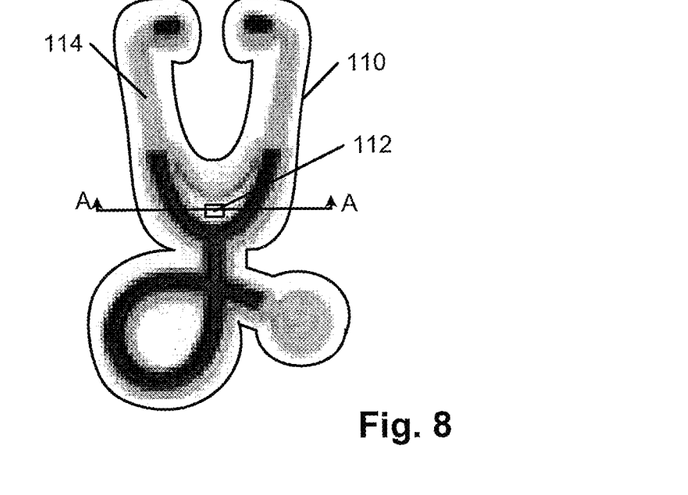
FIG. 8 illustrates an example a top view of an example basket designed to hold a stethoscope.
Figure 9:
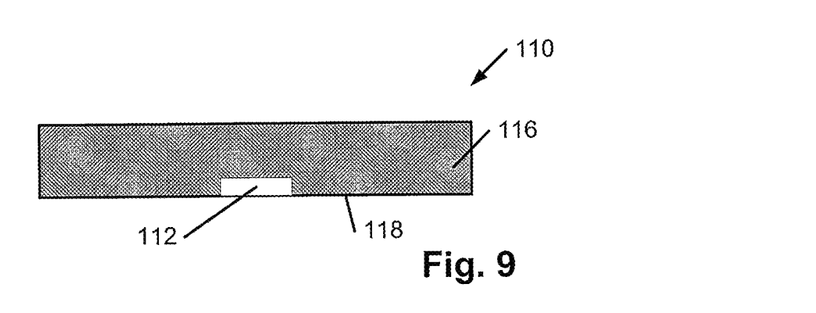
FIG. 9 illustrates a cross-sectional view of the example basket shown in FIG. 8 taken along axis A-A.

Further to the idea of ensuring objects placed in a cabinet are those that have been deemed suitable for a particular disinfection system, support structures are provided which are configured to confirm an object placed thereon is suitable for a particular disinfection system. In particular, support structures are provided which include a base with transparent materials and/or one or more through-holes and sidewalls shaped to match a peripheral contour of a particular object, such as a medical device. The sidewalls may be sidewalls of the base only or may extend up from the base. The configuration of the sidewalls to match a peripheral contour of a particular object offers visual confirmation that the object has been deemed suitable for the particular disinfection system the support structure comprises. In some cases, the support structure may additionally include contour sensors along its base and/or sidewalls to electronically confirm the peripheral contour of an object placed on the support structure matches that of the specifically shaped sidewalls. In any case, the support structure may include a shelf, basket or a tray. An example of a support structure having such features is illustrated in FIGS. 8 and 9. In particular, FIGS. 8 and 9 illustrate basket 110 having base 118 with transparent materials and/or one or more through-holes and sidewalls 116 shaped to match a peripheral contour of a stethoscope.

In some cases, the support structure may include a weight sensor, such as shown with weight sensor 112 in FIGS. 8 and 9, to verify whether the weight of an object placed on the support structure is in an appropriate range for what it has been designed to receive. In addition or alternatively, the support structure may include a scannable identification tag to coincide with a scanning identification system of a cabinet in which the support structure is to be arranged. In any of such cases, the support structure may, in some cases, include a means for conveying information to a user of the support structure (e.g., via visual display and/or audio commands) of the conditions of such various features. In some of such embodiments, the support structure may include a processor and a storage medium comprising program instructions executable by the processor for activating said means for conveying information upon receiving signal/s from the various features. For example, the support structure may include processor executable program instructions for activating said means for conveying information upon the weight sensor detecting a force that exceeds a predetermined threshold, upon a multiple of the contour sensors detecting contact with an object.

The term "storage medium", as used herein, refers to any electronic medium configured to hold one or more set of program instructions, such as but not limited to a read-only memory, a random access memory, a magnetic or optical disk, or magnetic tape. The term "program instructions", as used herein, refers to commands within software which are configured to perform a particular function. Program instructions may be implemented in any of various ways, including procedure-based techniques, component-based techniques, and/or object-oriented techniques, among others. Program instructions may be transmitted over or on a carrier medium such as a wire, cable, or wireless transmission link.

It will be appreciated to those skilled in the art having the benefit of this disclosure that this invention is believed to provide support structures, cabinets and methods for disinfecting objects. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A cabinet, comprising:
an interior void of at least 10 ft$^3$;
one or more alignment markers or an alignment system for placing an item in a predetermined position within the interior void;
one or more support structures arranged within one or more areas of the cabinet adjacent the interior void, wherein at least portions of the one or more support structures facing the interior void are transparent to germicidal light and/or comprise through-holes, and wherein the one or more support structures comprise shelving, one or more baskets and/or one or more trays; and
a door to enclose the cabinet.

2. The cabinet of claim 1, wherein the cabinet and/or at least one of the one or more support structures comprise an automated actuator for moving one or more objects placed on or in the one or more support structures.

3. The cabinet of claim 1, wherein at least one of the one or more support structures is moveably arranged within an interior of the cabinet.

4. The cabinet of claim 1, further comprising one or more loading ports extending through sidewalls of the cabinet in alignment with one of the one or more support structures.

5. The cabinet of claim 1, wherein one or more interior surfaces of the cabinet comprise a material exhibiting greater than 90% reflectance to at least ultraviolet light.

6. The cabinet of claim 1, further comprising a germicide dose sensor arranged within an interior of the cabinet.

7. The cabinet of claim 1, wherein at least one of the one or more support structures comprises a weight sensor.

8. The cabinet of claim 1, further comprising a scanning identification system.

9. The cabinet of claim 1, further comprising:
a power outlet along an interior surface of the cabinet for receiving a power plug; and
a power cord coupled to the power outlet and extending out from an exterior surface of the cabinet.

10. The cabinet of claim 1, wherein the door is for primarily accessing the interior void, and wherein the cabinet further comprises another door for primarily accessing the one or more areas in which the one or more support structures are arranged.

11. The cabinet of claim 1, wherein the cabinet is absent a floor.

12. The cabinet of claim 1, further comprising a floor with a tapered lip, wherein the door extends in proximity to the tapered lip.

13. A cabinet, comprising:
an interior void dimensionally configured to accommodate an object having a size of at least 10 ft$^3$, wherein a ceiling of the interior void comprises a material exhibiting greater than 85% reflectance to ultraviolet light and/or visible violet-blue light;
a first door for primarily accessing the interior void;
one or more support structures arranged within one or more areas of the cabinet adjacent the interior void, wherein at least portions of the one or more support structures facing the interior void are transparent to germicidal light and/or comprise through-holes, wherein the one or more support structures comprise shelving, one or more baskets and/or one or more trays;
one or more loading ports extending through sidewalls of the cabinet in alignment with one of the one or more support structures; and
a second door distinct from the first door, wherein the second door is for primarily accessing at least one of the one or more areas in which the one or more support structures are arranged.

14. The cabinet of claim 13, wherein the cabinet and/or at least one of the one or more support structures comprise an automated actuator for moving one or more objects placed on or in the one or more support structures.

15. The cabinet of claim 13, wherein at least one of the one or more support structures is moveably arranged within an interior of the cabinet.

16. The cabinet of claim 13, wherein one or more additional interior surfaces of the interior void comprise a material exhibiting greater than 85% reflectance to at least ultraviolet light.

17. The cabinet of claim 13, wherein at least one of the one or more support structures comprises a weight sensor.

18. The cabinet of claim 13, further comprising a scanning identification system.

19. The cabinet of claim 13, further comprising:
a power outlet along an interior surface of the cabinet for receiving a power plug; and
a power cord coupled to the power outlet and extending out from an exterior surface of the cabinet.

20. The cabinet of claim 13, wherein the cabinet is absent a floor.

21. The cabinet of claim 13, further comprising a floor with a tapered lip, wherein the first door extends in proximity to the tapered lip.

22. The cabinet of claim 13, wherein the second door is for primarily loading one or more objects onto the one or more support structures.

23. The cabinet of claim 13, further comprising:
a moveable partition for separating first and second portions of the cabinet, wherein the moveable partition is configured to block transmission of germicidal light; and
a sensor for detecting when the moveable partition is in position to separate the first and second portions of the cabinet.

24. A cabinet, comprising:
an interior void for receiving a particular disinfection device which is independently operational from the cabinet, wherein the cabinet does not comprise an electrical outlet or a battery for supplying power to the particular disinfection device;
one or more interior surfaces comprising a material exhibiting greater than 85% reflectance to ultraviolet light and/or visible violet-blue light;
a door to enclose the cabinet;
one or more support structures arranged within one or more areas of the cabinet adjacent the interior void, wherein at least portions of the one or more support structures facing the interior void are transparent to germicidal light and/or comprise through-holes, wherein the one or more support structures comprise shelving, one or more baskets and/or one or more trays, and wherein at least one of the one or more support structures has sidewalls shaped to match a peripheral contour of a medical object;

an object identification and/or analysis system configured to determine whether an object placed in the cabinet is suitable for disinfection in the cabinet by the particular disinfection device; and a user interface configured to communicate whether an object identified and/or analyzed by the object identification and/or analysis system is suitable for disinfection in the cabinet by the particular disinfection device.

25. The cabinet of claim 24, wherein the object identification and/or analysis system comprises a scanning identification system.

26. The cabinet of claim 24, wherein the object identification and/or analysis system comprises a weight sensor.

27. The cabinet of claim 24, wherein the object identification and/or analysis system comprises a contour sensor.

* * * * *